United States Patent [19]

Phillips

[11] Patent Number: 4,547,913

[45] Date of Patent: Oct. 22, 1985

[54] COMPOSITE PROSTHETIC FOOT AND LEG

[75] Inventor: Van L. Phillips, Salt Lake City, Utah

[73] Assignee: Flex Foot, Inc., Irvine, Calif.

[21] Appl. No.: 512,180

[22] Filed: Jul. 11, 1983

[51] Int. Cl.[4] .......................... A61F 1/00; A61F 3/00
[52] U.S. Cl. .................................. 623/27; 128/80 R; 623/29; 623/53
[58] Field of Search .................... 3/2, 4, 16, 21, 22, 3/29, 33, 35, 7, 6, 23, 25; 128/80 R, 80 A, 80 B, 80 E, 80 F

[56] References Cited

U.S. PATENT DOCUMENTS

| | | | |
|---|---|---|---|
| 366,494 | 7/1887 | Marks | 3/2 |
| 1,013,828 | 1/1912 | Thomas | 272/70.2 |
| 2,440,075 | 4/1948 | Campbell | 3/33 |
| 3,889,301 | 6/1975 | Bonner, Sr. | 3/21 X |
| 4,397,048 | 8/1983 | Brown et al. | 3/2 |

FOREIGN PATENT DOCUMENTS 25322  10/1922  France ...................... 3/7

Primary Examiner—Richard J. Apley
Assistant Examiner—Alan W. Cannon
Attorney, Agent, or Firm—Blakely, Sokoloff, Taylor & Zafman

[57] ABSTRACT

A composite prosthetic foot and leg which allows a high degree of mobility on the part of an amputee is disclosed. The prosthetic foot and leg utilizes a resin impregnated high strength filament structure for the leg portion, the foot portion and heel portion, with all three regions being provided with substantial elastic flexibility, preferably of relatively low energy absorption characteristics so as to give the wearer high mobility with a relatively natural feel. All three portions of the prosthetic foot and leg are rigidly joined, with a flexibility of the leg portion providing flexibility of the leg in response to both torques about the ankle as well as about a vertical axis while simultaneously providing sidewise rigidity of the structure. Various embodiments are disclosed.

14 Claims, 9 Drawing Figures

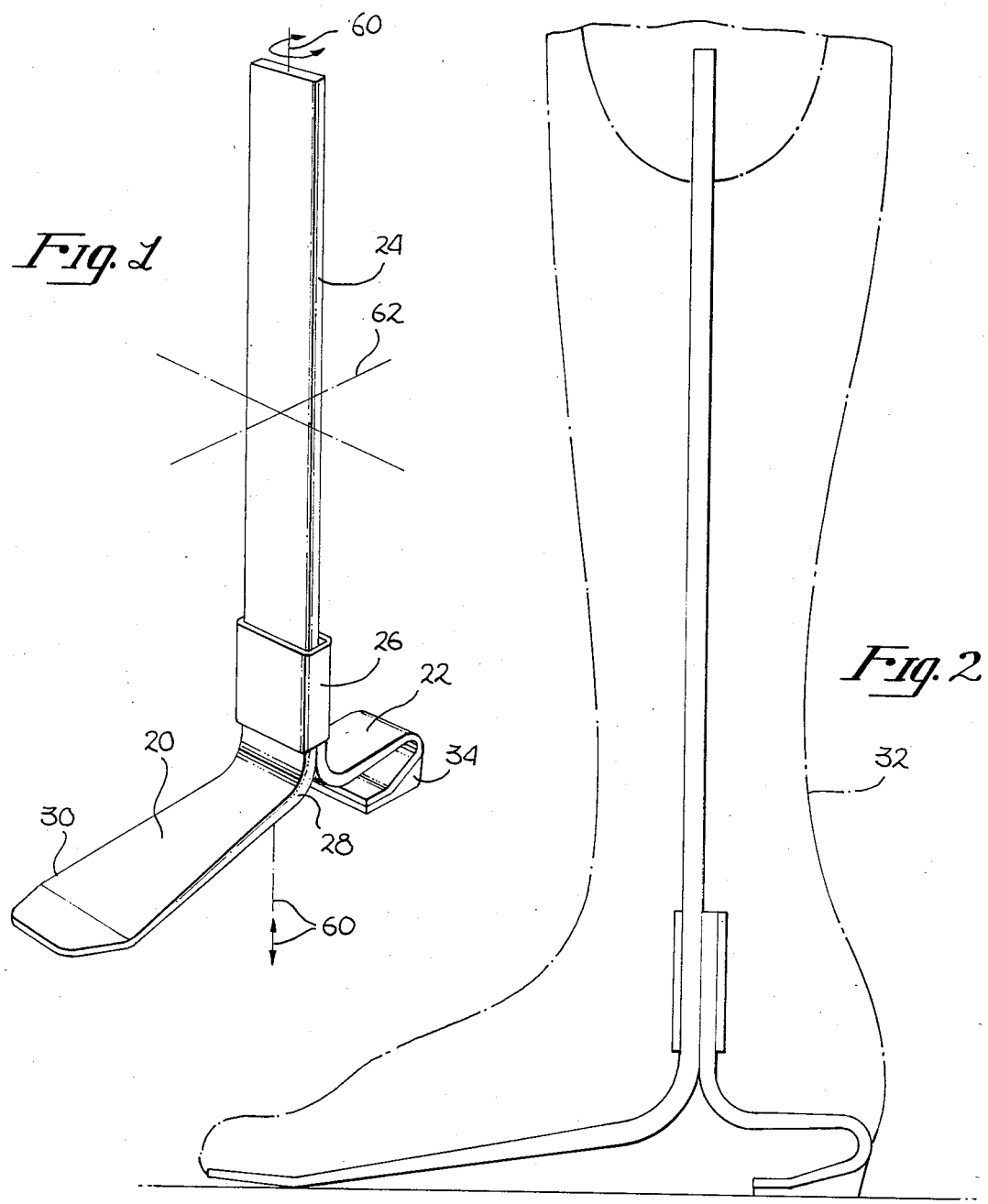

COMPOSITE PROSTHETIC FOOT AND LEG

BACKGROUND OF THE INVENTION

1. Field of the Invention

The present invention relates to prosthetic devices, and more particularly to prosthetic foot and leg devices.

2. Prior Art

Various types of foot and leg prosthetic devices are well known in the prior art. Such devices generally include some form of attachment for coupling the device to the dorsal end of the limb and for extending to the ground to provide body support. Such prosthetic devices, particularly those intended to mount below the knee, are now frequently fabricated as an assembly having a leg region and footlike region, with some form of pivot therebetween so as to allow the foot portion to assume various angles with the leg portion and vice versa, as the wearer walks or goes through conventional motions. Devices of this general type are shown in U.S. Pat. Nos. 2,379,538, 3,400,408, 4,007,496, 4,089,072 and 4,161,042. Some such prosthetic devices also include some rotatability between the foot portion and the connection to the limb, such as the ball joint of U.S. Pat. No. 3,400,408 and the swivel joint of U.S. Pat. No. 4,186,449. In general the leg and foot portions are usually rigid members, though frequently elastic energy absorbing members are also included to help absorb shock and for such other purposes as encouraging the ankle joint to a preferred position.

Also, various methods of attachment of a prosthetic device to the end of the limb are well known, the exact manner of attachment normally depending upon exactly where the limb has been severed and the surgical technique used to close the wound. In particular some surgical techniques result in a limb end which is particularly sensitive, and accordingly the proper fitting of a prosthetic device to such a limb requires both careful fitting and padding. Other techniques result in a limb end of relatively low sensitivity, allowing somewhat less of a custom fit of the prosthetic device to the limb. In any event, normally the prosthetic device is strapped to the limb to keep the prosthetic device in place throughout the wearer's normal motion, particularly when lifting the limb for walking and the like. Because of the relatively high weight of prior art prosthetic devices in comparison to the present invention, prior art devices require tighter strapping of the device to the limb, frequently restricting the blood flow in the limb. Generally speaking, because of the weight of prior art prosthetic devices and the fact that such devices are relatively stiff and if deflectable at all, are generally deflectable in an energy absorbing manner, the range of allowable activities of a wearer of prior devices is generally limited to relatively slow non-strenuous activities, such as walking, etc. More strenuous activity such as playing tennis and other sports, running, etc. is highly limited, as the weight of the prosthetic device, the shock of the device coming down on a hard surface and the inability of the prosthetic device to return the energy absorbed therein makes the more strenuous activities with such devices either impossible or uncomfortable and awkward.

BRIEF SUMMARY OF THE INVENTION

A composite prosthetic foot and leg which allows a high degree of mobility on the part of an amputee is disclosed. The prosthetic foot and leg utilizes a resin impregnated high strength filament structure for the leg portion, the foot portion and heel portion, with all three regions being provided with substantial elastic flexibility, preferably of relatively low energy absorption characteristics so as to give the wearer high mobility with a relatively natural feel. All three portions of the prosthetic foot and leg are rigidly joined, with the flexibility of the leg portion adding to the flexibility of the foot and heel portions in response to both torques about the ankle as well as about a vertical axis while simultaneously providing sidewise rigidity of the structure. Various embodiments are disclosed.

BRIEF DESCRIPTION OF THE DRAWINGS

FIG. 1 is a perspective view of one embodiment prosthetic foot and leg in accordance with the present invention.

FIG. 2 is a side view of the device of FIG. 1.

FIG. 3 is a bottom planform view of the device of FIG. 1.

DETAILED DESCRIPTION OF THE INVENTION

Figure 4:
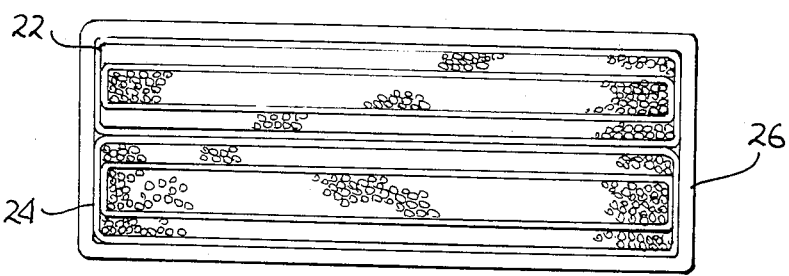
FIG. 4 is a cross section of the device of FIG. 1 taken through the ankle region thereof and FIGS. 5 through 9 are side views illustrating a few alternate embodiments of the present invention.

First referring to FIG. 1, a prospective view of one embodiment of the present invention may be seen. As is characteristic of the other embodiments of the present invention, the embodiment of FIG. 1 may be characterized as a "rigid" assembly in that the foot portion 20, the heel portion 22 and the leg portion 24 are all rigidly attached to each other at the ankle region by a binding 26, as opposed to having characteristic ankle pin or pivot, normally found in prior art prosthetic devices. The device of FIG. 1 is not rigid however, in that the high strength resin impregnated filament structure of the device, coupled with the specific geometry of the individual elements, provides substantial compliances in the device with respect to certain specific types of loads, and more particularly non-dissipative compliances, so that the energy put into the device during deflection is returned by the device as the deflection is removed, much like a taut muscle in combination with an ankle joint or the various foot bones would do.

In particular, both the foot portion 20 and the heel portion 22 are proportioned to serve as flat springlike members so that the foot and heel will provide both a strong cushioning effect and energy storage in response to vertical loads on the respective portion of the prosthetic device. In particular, the spring rates of these two members are purposely made relatively low so that the members, either operating alone or in conjunction with each other depending upon the exact direction of the load, will provide a very substantial non-energy absorbing compliance in the vertical direction. In that regard, it will be noted, by way of example, that the region 28 of the foot portion is thicker than the extremity 30 of the foot portion, which is desirable for a number of reasons. First, the planform of the foot portion 20, shown in FIG. 3 as a bottom view of the prosthetic device, more closely resembles the planform of an ordinary foot, thereby being more accomodating of a conventional shoe when worn in conjunction with a light foam rubber or other covering 32 shown in phantom in FIG. 2. In addition, however, the taper in thickness from the thicker region 28 to the thinner region 30 provides a thicker structure in the regions of higher bending moments. This has the dual effect of reducing the maximum stress of the foot portion, and of much better distribution of the deflection of the foot portion throughout a major portion of the length thereof to provide greater vertical compliance of the foot portion, particularly if the wearer has that knee forward to concentrate the weight supported by that leg entirely onto the toe region.

Figure 5:
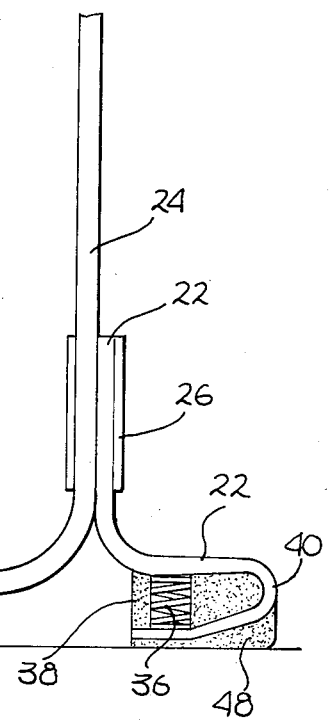

As previously stated, the heel portion 22 is also configured to intentionally provide natural flexibility in response to vertical loads, again in a substantially non-energy absorbing manner. Since the heel support is generally much closer to the ankle region at the lower end of the leg portion 24 than is the ground contact of the foot portion 20, the heel portion 22 is purposely formed as a U-shaped structure to provide greater length in the filament reinforced structure for increased compliance while maintaining overall load carrying capabilities. In the embodiment shown in FIGS. 1 and 2, an elastomeric heel pad 34 is used in addition for purposes of increasing the compliance. In that regard, tests to date with prototype prosthetic devices fabricated in accordance with the present invention indicate that the compliance readily obtainable in the toe portion 20 is approximately correct, but that the heel of the device and the mobility of the user may be even somewhat further enhanced by making the heel portion 22 even more compliant. This may be achieved by making the heel portion thinner so that the spring rate of the heel portion is lower, though the compliance which may be obtained in this manner alone appears limited because of the attendant increase in stress and corresponding reduction in load carrying capacity associated with the more compliant structure. The heel portion 22 may be made more compliant however, by making the filament reinforced structure thinner in the region of the bending to provide greater flexing capability, with some additional means being provided to share or carry the majority of the load without offsetting all of the increased compliance as a result of the thinner structure. By way of example, in FIG. 5 the heel portion 22 is further supported by a relatively low spring rate coil spring 36 maintained in place by an elastic or foam material 38. Actually, if desired, region 40 may be made quite a bit thinner than the remaining heel structure so as to effectively provide a flexure or hingelike member so that the overall spring rate of the heel portion is not much higher than the spring rate of spring 36.

Figure 6:
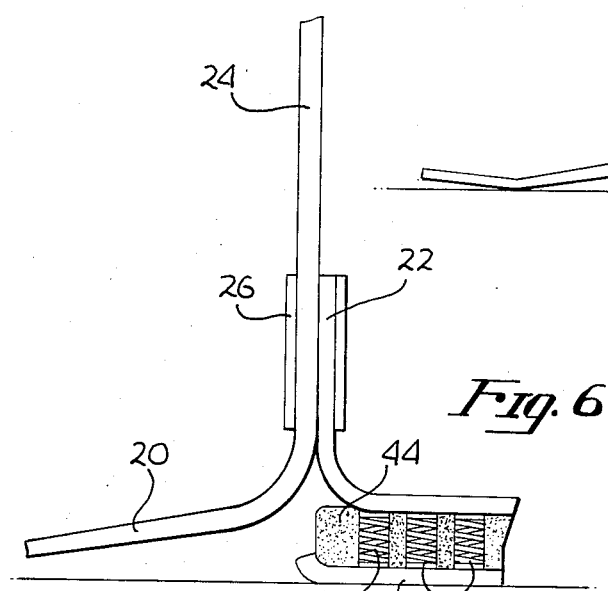
Figure 7:
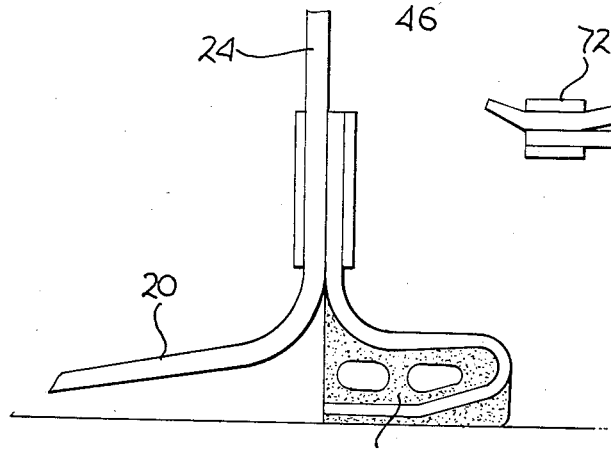

Additional embodiments showing alternate heel configurations may be seen in FIGS. 6 and 7. In particular, in FIG. 6 a plurality of springs 42 together with a foam or rubber retainer 44 are used, with a lower portion 46 of the heel portion not having a permanent lower elastomeric pad such as the elastomeric pad 48 of the embodiment of FIG. 5 thereon. Obviously of course the embodiment of FIG. 5 may be provided with two springs side by side, though the embodiment of FIG. 6 better distributes the load among a greater plurality of springs to provide the desired compliant support. Finally, in the embodiment of FIG. 7, a low energy loss rubber or elastomeric member 50 is used, the member being shaped and relieved to provide a stable structure with sufficient "squeeze" room to provide the compliance and the total deflection capabilities desired without potentially creating an over center or other type of energy dissipating structure.

Figure 9:
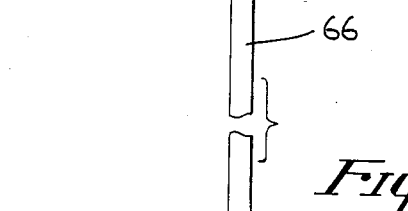

In FIG. 9, still another embodiment is shown which embodiment is also directed toward providing greater compliance in the heel portion. In particular, the leg portion 66 and foot portion 68 are fabricated as an integral structure as in the preferred embodiment of FIG. 1. However, unlike the structure of FIG. 1, the heel portion 70 is coupled to the leg and foot portions not in the ankle region, but rather toward the front of the foot, being coupled thereto by adhesive and a resin impregnated binding 72. Such a configuration effectively lengthens the structure giving rise to the heel compliance to provide substantially all the compliance one might reasonably desire for the heel portion without affecting the compliance of the foot portion.

Figure 8:
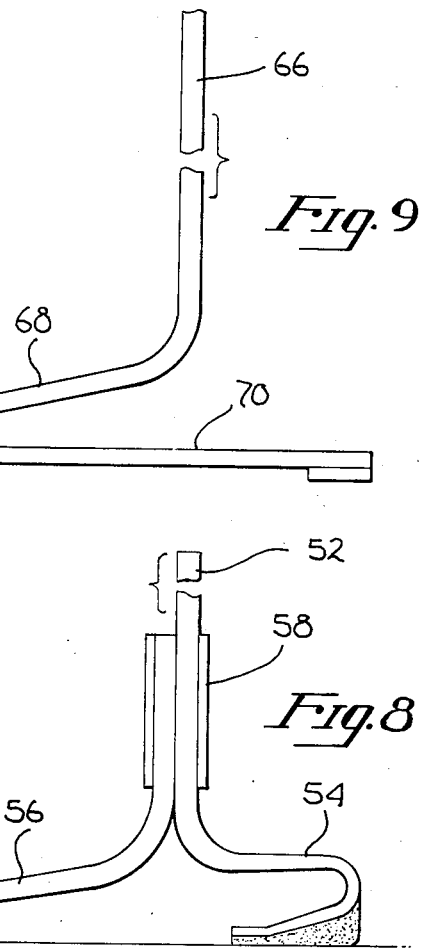

In the embodiment shown in FIGS. 1 through 3 and 5 through 7, the leg portion 24 and the foot portion 20 are formed as one member, with the vertical part of the heel portion being bonded and bound thereto with a resin impregnated filament binding 26. This of course is not a specific requirement however, as other methods may be used to provide an overall structure of the desired characteristics. By way of specific example, as shown in FIG. 8, the leg portion 52 may be formed integral with the heel portion 54, with foot portion 56 being cemented and bound thereto by a resin impregnated filament binding 58. As further alternate embodiments, the leg portion 52 could be split at approximately the ankle region so as to be integral with both the foot portion and the heel portion. A binding in the region of the split would still be used to prevent a progression of the split under load. As a still further alternative, the leg portion could be fabricated separate and apart from the heel and foot portions and subsequently attached thereto, though it is preferred to have at least one of the foot and heel portions represent a continuation of the leg portion for direct load transmission therebetween.

The preferred manner of fabrication of the prosthetic foot and leg is to use a combination of longitudinal (lengthwise) filaments in the leg, foot and heel portions interspersed with a fraction of transverse filament to bind the longitudinal filaments together and prevent separation thereof under load. A ratio of approximately 70 percent longitudinal or 90 degree filament and 30 percent transverse or 0 degree filament has been found suitable. The circularly wound filament may be interspersed with the longitudinal filament on at least two or more levels as illustrated in FIG. 4, the overall outer dimensions and form of the product in the uncured state, whether formed wet or formed dry and impregnated, being determined by a suitable mold in which the parts are held during curing of the resin.

Excellent results have been found using carbon filament with an epoxy binder. The first unit to be evaluated has a leg width of approximately two inches, a thickness of 0.3 inches, a toe length of 5.375 inches and a leg length of 12 inches (to be trimmed for fitting as required). The calculated maximum stress in the foot and heel regions for a 135 pound load is 25,286 psi in tension and compression (flexural stress) and 338 psi in sheer. The vertical spring rate of this first unit is approximately 735 pounds per inch, giving a deflection under a 135 pound static load of almost one-fifth of an inch. Obviously the deflection under dynamic loads such as during walking or even more vigorous activity such as running or playing tennis frequently are much higher. In that regard, because of the very low weight of the prosthetic foot and leg, the flexibility thereof and its ability to return energy put into the leg during deflection as the load thereon is decreased allows the user to participate in such sports as tennis in a very vigorous and effective manner.

While some prior art prosthetic foot and legs have used some degree of angular freedom at the ankle, by providing an appropriate bearing at that position, the present invention provides the same form of freedom by providing a substantial compliance about the vertical axis 60 (see FIG. 1) as a result of the cross section and length of the leg portion 24. In that regard, the first unit described above has a torsional spring rate about the vertical axis of approximately of 14 inch pounds per degree of rotation between the top of the leg portion and the foot and heel portions. Finally, it should be noted that the configuration of the leg portion of the preferred embodiments of the present invention, particularly the relatively high area moment of inertia of the cross section of the leg portion 24 taken along a longitudinal axis 62 and the relatively low area moment of inertia of the same cross section taken along a transverse axis 64, provides a very rigid structure about the axis 62 but substantial non-energy absorbing compliance about axis 64, which gives the prosthetic foot and leg some rotation capabilities as if it had an ankle joint. This compliance is of course limited though is sufficient to significantly enhance the performance thereof.

A second unit has also been fabricated and tested, this unit also being fabricated using epoxy impregnated carbon filament. The second unit also has a width of two inches, but a slightly thicker leg of 0.32 inches. The second unit has a total length of 5.75 inches, a leg length of 13 inches, a maximum stress for 135 pound load of 23,684 psi in flexing and 316 psi in sheer. The vertical spring rate of the second unit is 772 pounds per inch with the torsional spring rate being 15.6 inch pounds per degree.

Both prototype devices have given excellent results during the testing thereof. Both are very lightweight, consuming less energy of the user, reducing loads applied to the dorsal end of the severed limb and allowing substantial reduction of the strapping tension to hold the prosthesis to the limb. This substantially aids in the comfort of the user and permits normal blood circulation in the limb. While the two embodiments fabricated to date have been fabricated using carbon filament, other filament types may also be used such as glass, Kevlar and nylon, by way of example, to ensure lightweight and structural and dynamic characteristics consistent with the amputee. In that regard, the strength and stiffness of the device can be tailored to demand in each axis of freedom independently by simple dimensional and/or dimension ratio changes, thus simulating multiple axis muscle systems in a natural ankle and foot. Also the differences in filament types (carbon, glass, etc.) substantially affect spring rates, giving a further degree of selection and control of the characteristics of the device.

The prosthetic foot and leg of the present invention, aside from providing a mobility heretofore unobtained with prior art prosthetic devices, has the advantage of no mechanical moving parts to wear out, require servicing, to corrode or to become entangled with clothing or any cosmetic cover. This, in combination with a waterproof cosmetic covering, allows the leg to double as a swimming, shower or beach leg.

The device of the present invention may be used in conjunction with such devices as a Nike air wedge heel to further increase its flexibility, and will fit inside a normal shoe, with a polyurethane or ethylene foot cover easily being shaped to most any shoe shape. Built-in spring action, which minimizes the shock to the limb, is believed to increase the health of the residual limb as a result of the contraction and relaxation of the limb muscles reacting with the flexing and rebounding of the prosthesis. The muscles in the limb when a typical prior art stiff prosthetic leg is used are passive, and merely aid in supporting the weight of the user within the socket. With the flexing leg and foot prosthesis of the present invention, the amputee is given the sensation of working the prosthesis and not just standing on it while his weight passes from one foot to the other enhancing both blood flow and muscle tone.

Obviously while preferred embodiments of the present invention has been disclosed and described in detail herein, it will be understood by those skilled in the art that various changes in form and detail may be made therein without departing from the spirit and scope of the invention.

I claim:

1. A prosthetic foot and leg comprising a composite structure formed from synthetic resin impregnated high strength filament, said prosthetic foot and leg having as the primary structural elements thereof a foot portion and a heel portion aligned in a fore and aft direction, and a leg portion extending substantially vertically therefrom, said foot, heel and leg portions all being substantially rigidly joined to each other at the ankle region, said foot portion extending downward and forward of said ankle region so as to have substantial low energy absorption compliance in response to vertical loads thereon, said heel portion extending downward and rearward of said ankle region, said heel portion also being flexible so as to have substantial low energy absorption compliance in response to vertical loads thereon, said leg portion having at least a part being substantially planar and extending substantially vertically with a cross section having a high area moment of inertia about an axis generally aligned with the fore and aft direction and a relatively low area moment of inertia about a horizontal axis perpendicular to the fore and aft direction, whereby said leg portion may elastically flex in a vertical fore and aft plane and not in a vertical transverse plane.

2. The prosthetic foot and leg of claim 1 wherein at least one of said foot and heel portions is formed as a continuation of the leg portion.

3. The prosthetic foot and leg of claim 2 wherein said foot portion is formed as a continuation of the leg portion.

4. The prosthetic foot and leg of claim 3 wherein said foot and leg portions are comprised of a substantial percentage of filaments substantially aligned with the length of said foot and leg portions.

5. The prosthetic foot and leg of claim 1 wherein said heel portion is provided with the low energy absorption compliance, at least in part, by spring means cooperatively disposed with respect to said resin impregnated high strength filament heel portion to aid in the load carrying compliance of said heel portion.

6. The prosthetic foot and leg of claim 5 wherein said spring means comprises, at least in part, at least one metal spring.

7. The prosthetic foot and leg of claim 5 wherein said spring means comprises, at least in part, an elastomeric member.

8. The prosthetic foot and leg of claim 1 wherein the ankle region includes a resin impregnated filament binding circumscribing the ankle region to bind said foot, heel and leg portions at the ankle region.

9. A prosthetic foot and leg comprising a composite structure formed from synthetic resin impregnated high strength synthetic filament, said prosthetic foot and leg having a foot portion and a heel portion together defining a fore and aft direction, and a leg portion extending substantially vertically therefrom, said foot, heel and leg portions all being substantially rigidly joined to each other at the ankle region, said foot portion extending downward and forward of said ankle region, said heel portion extending downward and rearward of said ankle region, said leg portion extending upward for joining to means for attaching said prosthetic foot and leg to the dorsal end of the user's limb, said leg portion having a region thereof having as its only structure a substantially vertically extending portion whch is substantially planar with a cross section having a high area moment of inertia about an axis generally aligned with the fore and aft direction and a relatively low area moment of inertia about a horizontal axis perpendicular to the fore and aft direction, whereby said leg portion may elastically flex in a vertical fore and aft plane, may flex in torsion about its vertical axis and not flex in a vertical transverse plane.

10. The prosthetic foot and leg of claim 9 wherein said foot portion is a thin spring-like member extending downward and forward of said ankle region so as to have substantial low energy absorption compliance in response to vertical loads thereon.

11. The prosthetic foot and leg of claim 9 wherein said heel portion is flexible and includes means for providing substantial low energy absorption compliance in response to vertical loads thereon.

12. The prosthetic foot and leg of claim 11 wherein said heel portion is provided with the low energy absorption compliance, at least in part, by spring means cooperatively disposed with respect to said resin impregnated high strength filament heel portion to aid in the load carrying compliance of said heel portion.

13. The prosthetic foot and leg of claim 12 wherein said spring means comprises, at least in part, at least one metal spring.

14. The prosthetic foot and leg of claim 12 wherein said spring means comprises, at least in part, an elastomeric member.

* * * * *